United States Patent [19]

Burns et al.

[11] Patent Number: 5,221,260
[45] Date of Patent: Jun. 22, 1993

[54] INNERLESS DILATATION BALLOON CATHETER

[75] Inventors: Matthew M. Burns, Orono; David W. Lodin, Maple Grove, both of Minn.

[73] Assignee: SciMed Life Systems, Inc., Maple Grove, Minn.

[21] Appl. No.: 748,255

[22] Filed: Aug. 21, 1991

Related U.S. Application Data

[63] Continuation-in-part of Ser. No. 596,573, Oct. 11, 1990, Pat. No. 5,085,636, which is a continuation of Ser. No. 297,078, Jan. 13, 1989, abandoned, and a continuation-in-part of Ser. No. 730,224, Jul. 15, 1991, which is a continuation of Ser. No. 337,272, Apr. 13, 1989, Pat. No. 5,032,113.

[51] Int. Cl.$^5$ ............................................. A61M 29/00
[52] U.S. Cl. ..................................... 604/99; 606/194
[58] Field of Search ........................... 604/96–103, 604/264, 280, 282; 606/192, 194

[56] References Cited

U.S. PATENT DOCUMENTS

| 3,402,717 | 8/1965 | Doherty . | |
|---|---|---|---|
| 3,675,658 | 7/1972 | Taylor | 128/349 BV |
| 3,707,151 | 12/1972 | Jackson | 128/351 |
| 3,726,283 | 4/1973 | Dye et al. | 128/349 BV |
| 4,085,757 | 4/1978 | Pevsner | 128/325 |
| 4,102,342 | 7/1978 | Akiyama et al. | 128/325 |
| 4,213,461 | 7/1980 | Pevsner | 128/348 |
| 4,456,000 | 6/1984 | Schjeldahl et al. | 128/1 D |
| 4,509,523 | 4/1985 | Pevsner | 128/658 |
| 4,598,707 | 7/1986 | Agdanowski et al. | 128/207.15 |
| 4,606,347 | 8/1986 | Fogarty et al. | 128/344 |
| 4,646,742 | 3/1987 | Packard et al. | 128/344 |
| 4,762,129 | 8/1988 | Bonzel | 128/344 |
| B1 4,762,129 | 7/1991 | Bonzel | 606/194 |
| 4,782,834 | 11/1988 | Maguire et al. | 128/344 |
| 4,811,737 | 3/1989 | Rydell | 128/344 |
| 4,813,934 | 3/1989 | Engelson et al. | 604/99 |
| 4,819,637 | 4/1989 | Dormandy, Jr. et al. | 128/325 |
| 4,820,262 | 4/1989 | Finney | 604/8 |
| 4,820,349 | 4/1989 | Saab | 128/344 |
| 4,846,174 | 6/1989 | Willard et al. | 128/344 |
| 4,848,344 | 7/1989 | Sos et al. | 128/344 |
| 4,877,031 | 10/1989 | Conway et al. | 128/344 |
| 4,932,959 | 6/1990 | Horzewski et al. | 606/194 |
| 4,944,745 | 7/1990 | Sogard et al. | 606/194 |
| 5,032,113 | 7/1991 | Burns | 604/96 |
| 5,059,176 | 10/1991 | Winters | 604/96 |
| 5,061,273 | 10/1991 | Yock | 606/194 |
| 5,085,636 | 2/1992 | Burns | 604/99 |
| 5,100,385 | 3/1992 | Bromander | 604/99 |

Primary Examiner—John D. Yasko
Assistant Examiner—Adam J. Cermak
Attorney, Agent, or Firm—Kinney & Lange

[57] ABSTRACT

An "innerless" balloon catheter controls fluid flow past the guide wire at the distal end of the catheter by a combination of flow resistance and a pressure responsive valve. The catheter includes a shaft which carries an inflatable balloon at its distal end. The shaft has a lumen therethrough with the lumen being in fluid communication with the balloon interior for inflating and deflating the balloon via the shaft lumen. The catheter further includes a lumen extension through the balloon, with the lumen extension being in fluid communication with the shaft lumen. A guide wire extends through the shaft lumen and the lumen extension and out the distal end of the balloon. The resistance to fluid flow past the guide wire in the lumen extension is substantially greater than the resistance to fluid flow between the shaft lumen and the balloon interior. A valve member is responsive to the pressure in the balloon interior for blocking fluid flow through the lumen extension during continuing inflation and at least the initial deflation of the balloon.

16 Claims, 2 Drawing Sheets

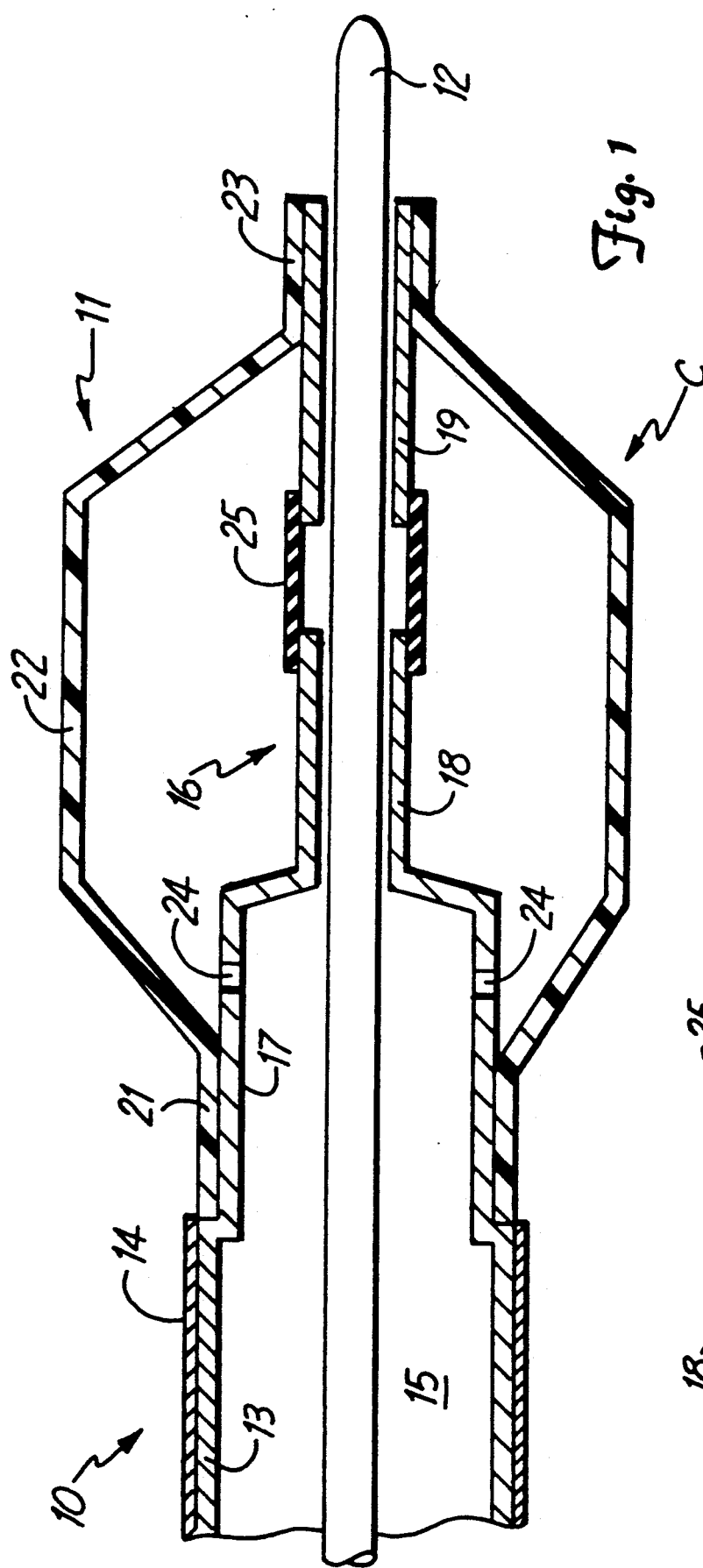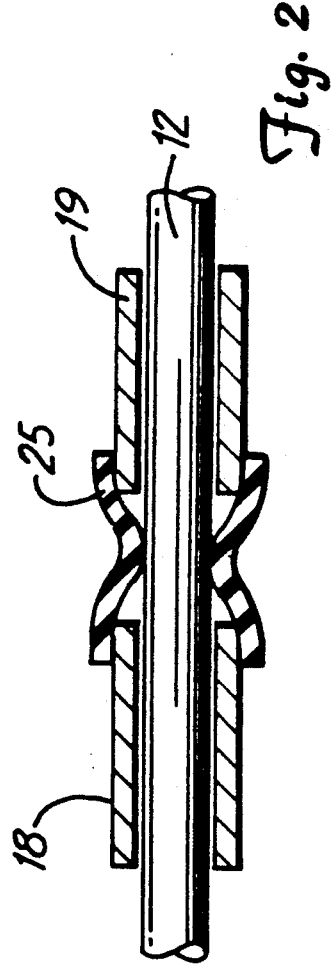

INNERLESS DILATATION BALLOON CATHETER

This application is a continuation-in-part of U.S. patent application Ser. No. 07/596,573 filed Oct. 11, 1990 by Matthew M. Burns, now U.S. Pat. No. 5,085,636 which is a continuation of Ser. No. 07/297,078 filed Jan. 13, 1989 (now abandoned); and continuation-in-part of patent application Ser. No. 07/730,224 filed Jul. 15, 1991 by Matthew M. Burns which is a continuation of Ser. No. 07/337,272 filed Apr. 13, 1989 (now issued as U.S. Pat. No 5,032,113). All of the above-mentioned applications are assigned to the same assignee as the present application, and are hereby incorporated by reference.

BACKGROUND OF THE INVENTION

The present invention relates to angioplasty and, in particular, to a dilatation balloon catheter.

Angioplasty has gained wide acceptance in recent years as an efficient and effective method for treating types of vascular diseases. In particular, angioplasty is widely used for opening stenoses in the coronary arteries. It is also used for treatment of stenoses in other parts of the vascular system.

A common form of angioplasty makes use of a dilatation catheter which has an inflatable balloon at its distal end. With the aid of fluoroscopy, a physician guides the catheter through the vascular system until the balloon is positioned across the stenosis. The balloon is then inflated by supplying fluid pressure through an inflation lumen to the balloon. Inflation of the balloon causes stretching of the artery and a pressing of the lesion into the artery wall to reestablish acceptable blood flow through the artery.

It is apparent that treatment with a dilatation catheter requires that the catheter reach and cross a stenosis. In order to extend treatment to very tight stenosis with small openings, there has been a continuing effort to reduce the profile (and shaft diameter) of the catheter. In addition, a successful dilatation catheter must be sufficiently flexible to pass through tight curvatures through the very tortuous path of the vascular system.

A further requirement of a successful dilatation catheter is its "pushability." This involves a transmission of longitudinal force along the catheter from its proximal end to its distal end so that a physician can push the catheter through the vascular system and the stenosis.

It is a common practice to employ a guide wire to establish the path to the stenosis. The dilatation catheter is then fed over the guide wire until the balloon is positioned within the stenosis. As an alternative, the catheter can serve as its own guide wire. One disadvantage to the self-guiding approach is that there is nothing to maintain the desired position within the vascular system when replacing the catheter—as when a larger or smaller balloon is desired, for example. Such replacement requires that the path to the stenosis must be reestablished when the catheter is replaced.

The use of a catheter assembly employing a guide wire provides the advantage of maintaining a path to the stenosis during a catheter exchange. One problem with many so-called "over-the-wire" catheters is the need to accommodate the guide wire within the catheter which has often been accomplished through the provision of a separate guide wire lumen. This has resulted in a larger profile (and shaft) to allow for the separate guide wire lumen.

SUMMARY OF THE INVENTION

The present invention is an "innerless" balloon catheter which uses a combination of resistance to fluid flow past a guide wire and a fluid pressure responsive valve to control fluid flow during inflation and deflation of the balloon. The catheter includes a shaft which carries an inflatable balloon at its distal end. The shaft has a lumen which is in fluid communication with the balloon interior. The shaft lumen also accommodates the guide wire without a provision for a separate guide wire lumen through at least a substantial portion of the catheter shaft.

In accordance with the present invention, a lumen extension extends through the balloon, with the lumen extension being in fluid communication with the shaft lumen. A guide wire extends through the shaft lumen and the lumen extension and out the distal end of the balloon. The resistance to fluid flow past the guide wire in the lumen extension is substantially greater than the resistance to fluid flow between the shaft lumen and the balloon interior. A valve responds to the pressure in the balloon interior for blocking fluid flow through the lumen extension during continuing inflation of the balloon and at least the initial deflation of the balloon interior. In a preferred embodiment, the valve is formed as a resilient member within the lumen extension, and surrounds the guide wire within the lumen extension to engage the guide wire when the balloon interior is pressurized.

BRIEF DESCRIPTION OF THE DRAWINGS

FIG. 1 is a partial sectional view of a preferred embodiment of a portion of a balloon catheter assembly in accordance with the present invention.

FIG. 2 is a partial sectional view showing in detail the cooperation between the valve member illustrated in FIG. 1 and the guide wire when the balloon interior is pressurized.

DETAILED DESCRIPTION OF THE PREFERRED EMBODIMENTS

Figure 3:
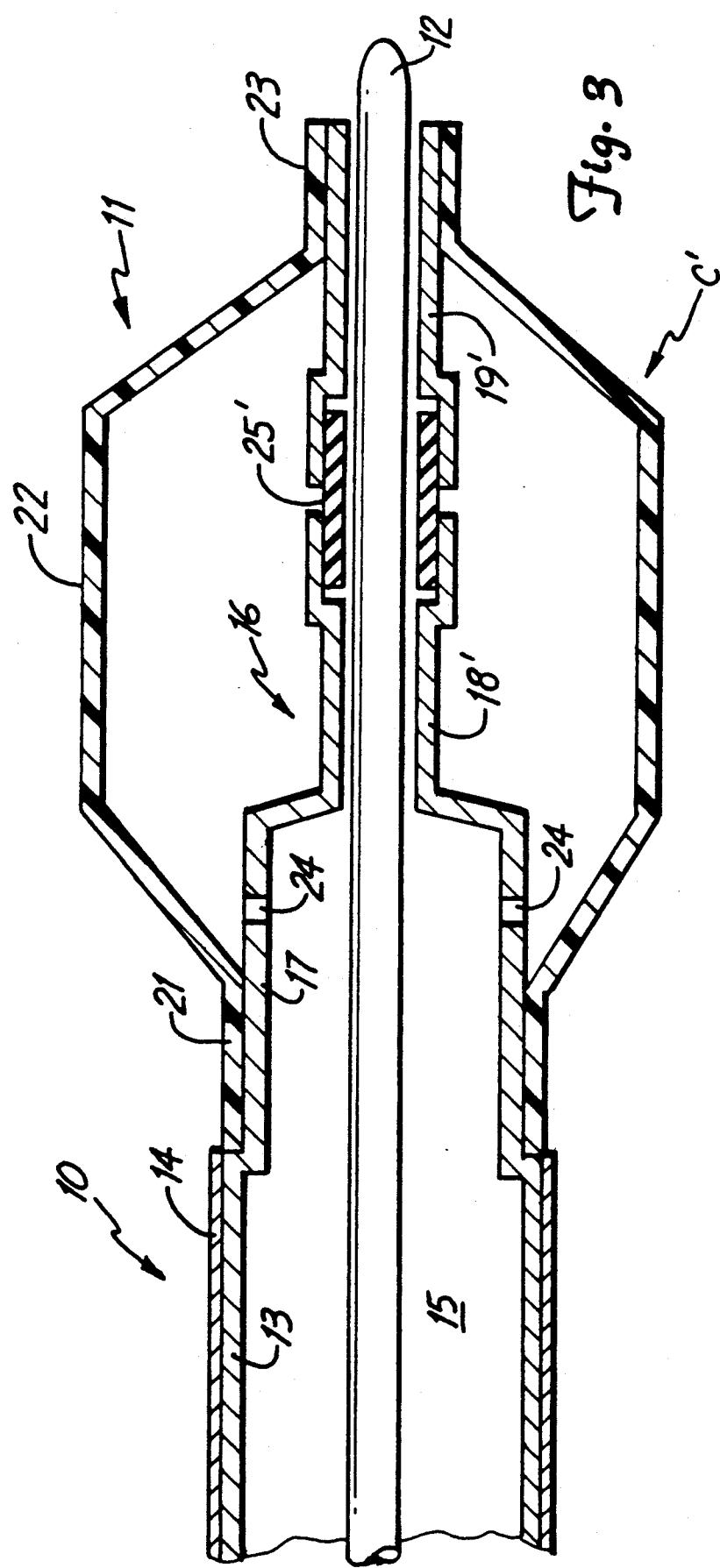
FIG. 3 is a partial sectional view of a further preferred embodiment of a portion of a balloon catheter assembly in accordance with the present invention.

An over-the-wire dilatation catheter necessarily requires a passage for the guide wire with an opening of the passage at the distal end of the catheter having a potential for fluid communication between the patient's body and catheter lumen. When the guide wire extends through a dedicated guide wire lumen which is not pressurized or depressurized during inflation and deflation of the balloon, this guide wire opening poses little difficulty. However, in an "innerless" catheter in which the guide wire extends through the same lumen which is used for inflation/deflation of the balloon, a control of fluid flow between the catheter and the patient's body is at least desirable, if not necessary in order to achieve reliable inflation and deflation of the balloon. The present invention provides this control through the use of a lumen extension which passes through the balloon and which controls fluid flow by the combined effects of a resistance to fluid flow resulting from a desired cooperation between the guide wire and lumen extension and the action of a valve member responsive to fluid pressure in the balloon interior. The valve member is active during continuing inflation of the balloon as well as during at least the initial deflation of the balloon.

FIG. 1 is a sectional view showing the distal end of a balloon catheter C in accordance with the present invention. Catheter C includes catheter shaft 10 and balloon 11, and is used in conjunction with guide wire 12. Shaft 10 is formed of an elongated flexible tube 13, preferably a stainless steel or polyamide with a low friction coating 14 such as PARALENE (poly p-xylene) or TEFLON (PTFE fluorocarbon). Depending on the characteristics desired, shaft 10 can be of an integral or multi-part construction. In one embodiment, shaft 10 has an inside diameter of about 0.027 inch and outside diameter of about 0.031 inch, and a shaft coating 14 thickness of about 0.0008 inch. Shaft 10 is mounted at its proximal end to an inflation device (not shown) which provides fluid under pressure to lumen 15 of shaft 10 for balloon inflation. Lumen 15 serves as a passage for fluid as well as for guide wire 12.

Lumen extension 16 extends from the distal end of shaft 10. Lumen extension 16 includes a proximal portion formed by shoulder section 17 and intermediate section 18 and a distal portion formed by stub section 19. Each section is generally cylindrical, with sections 18 and 19 being of a diameter less than that of shoulder section 17. As can be seen in FIG. 1, lumen extension 16 extends through balloon 11.

Balloon 11, which is preferably a polymer material such as polyolefin, has a proximal or waist segment 21, a distensible balloon segment 22 and a small diameter distal segment 23. Waist segment 21 is bonded to shoulder section 17 of the lumen extension, while distal segment 23 of balloon 11 is bonded to the stub section 19. Perforations 24 through shoulder section 17 of lumen extension 16 provide ports for inflation/deflation of balloon 11 by control of the pressure in shaft lumen 15.

Shoulder section 17 and intermediate section 18 of lumen extension 16 are shown integrally formed with tube 13 of shaft 10. Alternatively, those sections may be separately formed of a suitable material with appropriate securement to achieve the relationships indicated in FIG. 1.

Intermediate section 18 and distal section 19 of lumen extension 16 are shown spaced from each other to form a "break" within lumen extension 16. Sections 18 and 19 of lumen extension 16 are generally cylindrical with the break extending around the entirety of the periphery of lumen extension 16. Valve member 25 spans the break in lumen extension 16 and is suitably secured to lumen extension 16 such that the break is sealed and the integrity of the balloon interior is maintained. Valve member 25 is preferably made of a flexible polymeric material such that inflation/pressurization of balloon 11 causes a deflection of valve member 25 into and through the break in lumen extension 16 and into engagement with guide wire 12 as will be described further with respect to FIG. 2.

As is typical of over-the-wire catheters, guide wire 12 extends through shaft 10 and balloon 11 and out the distal end of catheter C. The opening in the balloon through which guide wire 12 extends provides an opening for fluid flow through lumen extension 16 between shaft lumen 15 and the exterior of catheter C. In the present invention, this fluid exchange is controlled, in part, by configuring lumen extension 16 and guide wire 12 such that the resistance to fluid flow through lumen extension 16 with guide wire 12 in place is significantly higher than the resistance to fluid flow between shaft lumen 15 and the interior of balloon 11, via perforations 24. Thus, when shaft lumen 15 is pressurized, balloon 11 will inflate. Similarly, the fluid within the interior of balloon can be withdrawn via shaft lumen 15 to deflate balloon 11.

In accordance with the present invention, fluid flow through lumen extension 16 is further controlled via valve member 25, which responds to the pressure in the interior of balloon 11 causing it to converge toward guide wire 12 (through the break in the lumen extension 16 formed by sections 18 and 19) until valve member 25 engages the guide wire 12 as shown in FIG. 2. This positive control of fluid flow through lumen extension 16 is initiated when fluid pressure in the interior of balloon 11 reaches a threshold value and continues during continued inflation of the balloon. The positive control of fluid flow through the lumen extension 16 via valve member 25 will also be continued during at least the initial deflation of the interior of the balloon 11; that is, until the pressure within the interior of balloon 11 decreases below the threshold value and no longer acts sufficiently on valve member 25 to extend it into contact with guide wire 12. During contact between valve member 25 and guide wire 12, axial movement of catheter C relative to the guide wire 12 is restricted. On the other hand, when fluid pressure is not being applied, guide wire 12 and catheter C can move freely with respect to one another.

The particular flow characteristics necessary to accomplish the stated purposes are dependent on the size of perforations 24 and the relative sizes and deforming characteristics of the materials forming balloon 11, including valve member 25, but are within the abilities of one ordinarily skilled in the art given the design criteria stated herein and the teachings of the above-incorporated patent applications.

Figure 4:
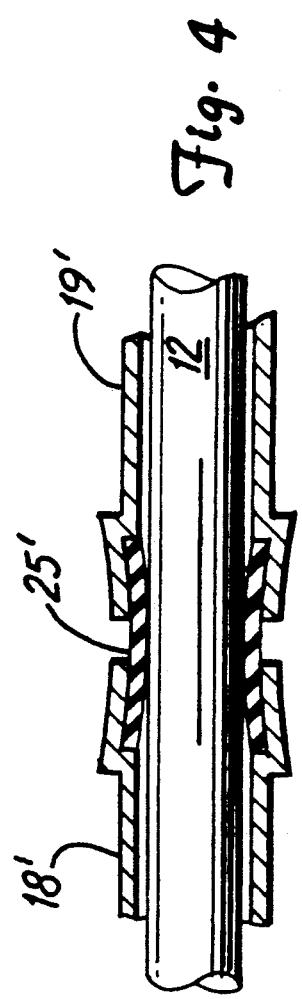
FIG. 4 is a partial sectional view showing in detail the cooperation between the valve member illustrated in FIG. 3 and the guide wire when the balloon interior is pressurized.

FIGS. 3 and 4 show an alternative embodiment to that illustrated in FIGS. 1 and 2. Throughout the figures, like elements are designated by identical reference numerals. The primary difference in catheter C' of FIGS. 3 and 4 to catheter C of FIGS. 1 and 2 is in the formation of the break in the lumen extension 16 and the manner in which valve member 25 spans that break. As shown in FIGS. 3 and 4, each of sections 18' and 19' are formed with opposing enlarged or cup-shaped portions which open toward each other and whose termini define the break in lumen extension 16. That break is spanned by valve member 25' which is similar in construction to the valve member 25 of FIGS. and 2 but which is smaller in diameter, the diameter of valve member 25' corresponding to the diameter of the main body of sections 18' and 19'. Valve member 25' is supported so that it is nonetheless responsive to pressure within the interior of balloon 11 such that pressure within balloon 11 causes valve member 25' to compress and engage guide wire 12 as illustrated in FIG. 4. In the embodiment of FIGS. 3 and 4, flow restriction through lumen extension 16 is established on placement of the guide wire 12 with valve member 25' being active during continuing inflation and at least the initial deflation of the interior of balloon 11, as described above with reference to FIGS. 1 and 2.

Many modifications and variations of the present invention are possible in light of the above teachings. That is, the present invention provides a control of fluid flow from and to an over-the-wire catheter through the combined effects of a flow restriction established by the positioning of the guide wire through the catheter, and by an active valve element responsive to pressure within the balloon interior to act on the guide wire. Pressure responsive valve elements other than those specifically shown can be easily accommodated within the present invention. Further, the drawings are for purposes of illustration only and are not necessarily drawn to scale. It is therefore to be understood that, within the scope of the appended claims, the invention may be practiced otherwise than as specifically described.

What is claimed is:

1. A balloon catheter assembly comprising:
   a shaft having a proximal end, a distal end, and a lumen which extends between the proximal end and the distal end;
   a balloon carried at the distal end of the shaft, the balloon having an interior which is in fluid communication with the lumen to permit inflation and deflation of the balloon;
   a guide wire;
   a lumen extension through the interior of the balloon, the lumen extension being fixed to the distal end of the shaft to provide a passage for the guide wire to extend through the shaft and the balloon, the lumen extension having an inner diameter which permits relative movement of the guide wire and the balloon catheter and which provides a resistance to fluid flow past the guide wire in the lumen extension which is greater than resistance to fluid flow between the lumen and the interior of the balloon during at least a part of the inflation of the balloon; and
   valve means responsive to pressure in the interior of the balloon for blocking fluid flow through the lumen extension during at least a part of inflation and deflation of the balloon.

2. The balloon catheter assembly of claim 1 wherein the valve means comprises a flexible tube positioned within the interior of the balloon which has an outer surface exposed to fluid pressure within the interior of the balloon, the flexible tube having an inner surface which defines a portion of the lumen extension and which engages the guide wire to block fluid flow through the lumen extension when pressure on the outer surface is greater than the threshold value.

3. The balloon catheter assembly of claim 2 wherein the lumen extension includes a proximal portion connected to the shaft and a distal portion connected to a distal end of the balloon.

4. The balloon catheter assembly of claim 3 wherein the flexible tube extends between the proximal portion and the distal portion.

5. The balloon catheter assembly of claim 4 wherein the proximal portion has a first pocket at a distal end and the distal portion has a second pocket at a proximal end, and wherein the flexible tube has a first end positioned in the first pocket and a second end positioned in the second pocket.

6. A balloon catheter assembly comprising:
   an inflatable balloon;
   a shaft which carries the inflatable balloon at a distal end of the shaft, the shaft having a lumen therethrough with the lumen being in fluid communication with an interior of the balloon for inflation and deflation of the balloon via the lumen;
   a lumen extension through the balloon, the lumen extension being in fluid communication with the lumen;
   a guide wire movably extending through the lumen and the lumen extension, wherein resistance to fluid flow past the guide wire in the lumen extension is greater than resistance to fluid flow between the lumen and the interior of the balloon during at least a part of the inflation of the balloon; and
   valve means responsive to the pressure in the interior of the balloon for limiting fluid flow through the lumen extension during at least a part of the inflation and deflation of the balloon.

7. The balloon catheter assembly of claim 6 wherein the valve means comprises resilient means within the lumen extension and surrounding the guide wire within the lumen extension.

8. The balloon catheter assembly of claim 7 wherein the lumen extension includes a tubular portion having an annular break, the resilient means comprising a flexible ring generally coaxial with the lumen extension and spanning said break.

9. The balloon catheter assembly of claim 6 wherein the lumen extension includes a tubular portion having an annular break; and the valve means is located at the break.

10. An over-the-wire angioplasty balloon catheter assembly comprising:
    a shaft having a proximal end and a distal end, and having a lumen extending therethrough from the proximal end to the distal end;
    an inflatable balloon at the distal end of the shaft with its interior in fluid communication with the lumen, and with the balloon having a proximal segment, an intermediate expandable segment and a distal segment;
    a guide wire movably extending through the lumen of the shaft and the balloon interior;
    a lumen extension fixed to the distal end of the shaft and the distal segment of the balloon for defining a path for the guide wire through the balloon and out of the balloon through the distal segment thereof; and
    valve means, positioned across the path, which permits movement of the guide wire freely therethrough for providing a fluid restriction around the guide wire and across the path during at least a part of inflation and deflation of the inflatable balloon.

11. An over-the-wire angioplasty balloon catheter assembly comprising:
    a shaft having a proximal end and a distal end, and having a lumen extending therethrough from the proximal end to the distal end;
    an inflatable balloon at the distal end of the shaft with its interior in fluid communication with the lumen, and with the balloon having a proximal segment, an intermediate expandable segment and a distal segment;
    a guide wire movably extending through the lumen of the shaft and the balloon interior;
    a lumen extension connected to the distal end of the shaft and the distal segment of the balloon for defining a path for the guide wire through the balloon and out of the balloon through the distal segment thereof, the lumen extension having an inner diameter which is greater than an outer diameter of the guide wire to permit relative axial movement of the guide wire and the lumen extension and to define a passage around the guide wire in the lumen extension which has a resistance to fluid flow that is substantially greater than resistance to fluid flow between the lumen and the interior of the balloon during at least part of the inflation of the balloon; and valve means, positioned across the path, which permits movement of the guide wire freely therethrough for providing a fluid restriction around the guide wire and across the path only when positive fluid pressure is applied through the lumen to the interior of the balloon.

12. A balloon catheter assembly comprising:

a shaft having a proximal end and a distal end, and having an inflation lumen extending therethrough from the proximal end to the distal end;

a lumen extension having a proximal end fixed to the distal end of the shaft, and a distal end, the lumen extension extending distally from the shaft;

a guide wire movably extending through the inflation lumen and the lumen extension;

an inflatable balloon at the distal end of the shaft with an interior in fluid communication with the inflation lumen, the balloon surrounding the lumen extension and being connected to the distal end of the lumen extension;

valve means responsive to fluid pressure in the interior of the balloon for providing an essentially fluid-tight seal around the guide wire during inflation and deflation of the balloon; and wherein the lumen extension has an inner diameter which permits relative movement of the guide wire and the balloon catheter and which provides a resistance to fluid flow past the guide wire in the lumen extension which is greater than resistance to fluid flow between the lumen and the interior of the balloon during at least a part of the inflation of the balloon.

13. The catheter assembly of claim 12 wherein the lumen extension has a port communicating between the lumen and the interior of the balloon.

14. The catheter assembly of claim 12 wherein the balloon member has a proximal segment, and intermediate balloon segment, and a distal segment.

15. The catheter assembly of claim 14 wherein the valve means is located within the intermediate balloon segment.

16. The catheter assembly of claim 12 wherein the valve means comprises a flexible tube which surrounds the guide wire and which deforms radially inwardly in response to fluid pressure in the interior of the balloon.

* * * * *